United States Patent [19]

Sugihara et al.

[11] Patent Number: 4,736,031
[45] Date of Patent: Apr. 5, 1988

[54] 2-(PIPERAZINYLALKYL)-1-BENZOTHIE-PIN, 1-BENZOXEPIN, AND 1,5-BENZODIOXEPIN DERIVATIVES

[75] Inventors: Hirosada Sugihara; Minoru Hirata, both of Osaka, Japan

[73] Assignee: Takeda Chemical Industries, Ltd., Osaka, Japan

[21] Appl. No.: 852,214

[22] Filed: Apr. 15, 1986

[30] Foreign Application Priority Data

Jun. 10, 1985 [JP] Japan .................. 60-126625

[51] Int. Cl.$^4$ ................. C07D 241/04; A61K 31/495; A61K 31/335; A61K 31/38
[52] U.S. Cl. ..................... 544/376; 540/596; 544/377; 546/196; 546/197; 546/202; 548/525; 548/526; 549/9; 549/10; 549/350; 549/355
[58] Field of Search ............... 540/596; 544/376, 377; 546/196, 197, 202; 548/525, 526; 549/9, 10, 350, 255; 514/212, 320, 321, 324, 422, 431, 450, 253

[56] References Cited

U.S. PATENT DOCUMENTS

| | | | |
|---|---|---|---|
| 3,306,913 | 2/1967 | Augstein et al. | 549/350 |
| 3,517,031 | 6/1970 | Beereboom et al. | 514/450 |
| 3,584,002 | 6/1971 | Williams et al. | 549/350 |
| 3,647,479 | 3/1972 | Beereboom et al. | 514/450 |
| 4,188,390 | 2/1980 | Campbell | 549/350 |

OTHER PUBLICATIONS

Thompson et al., Stroke, vol. 15, No. 6, 1984, pp. 1021-1024.
Bevan et al., Blood Vessels, vol. 21, 1984, pp. 201-203.
Cree et al., Agents and Actions, vol. 16, No. 5, 1985, pp. 313-317.
Wenting et al., "5-Hydroxytryptamine and Blood Pressure", Univ. Hosp. Dij Kzigt, Netherlands, Jul. 28, 1983, pp. 100-109.
Cohen et al., Journal of Pharmacology and Exp. Therapeutics, vol. 227, No. 2, U.S.A., 1983, pp. 327-332.
Clerek et al., Thrombosis Research, vol. 27, 1982, U.S.A., pp. 713-727.
Stewart et al., The Lancet, Gartnaval Gen. Hosp., Glasgow, Scotland, Aug. 27, 1983, pp. 479-481.
Sorkin et al., Univ. of Mich., 1982, pp. 1255-1261.
Clerck et al., Agents and Actions, vol. 12, No. 3, 1982, pp. 388-397.
Bevan et al., Thrombosis Research, vol. 30, 1983, pp. 415-423.
Demoulin et al., The Lancet, Univ. Hosp., B-4020 Liègel Belgium, May 30, 1981, pp. 1186-1188.
Phosphorus and Sulfur 14, 151-156 (1983).
Federation Proceedings 42, 182-185 (1983).

Primary Examiner—Henry R. Jiles
Assistant Examiner—J. G. Mullins
Attorney, Agent, or Firm—Wegner & Bretschneider

[57] ABSTRACT

Novel condensed seven-membered heterocyclic compounds of the formula:

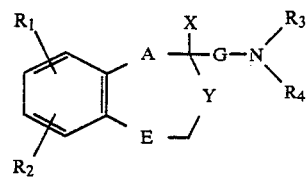

wherein
$R_1$ and $R_2$ are independently hydrogen, halogen, hydroxy, lower alkyl or lower alkoxy,
$R_3$ and $R_4$ are independently hydrogen, optionally substituted lower alkyl, optionally substituted cycloalkyl or optionally substituted aralkyl, or both jointly form an optionally substituted ring together with the adjacent nitrogen atom,
X is hydrogen, optionally substituted lower alkyl, optionally substituted aryl or a carboxyl group which may be esterified or amidated,
Y is $>C=O$ or $>CH-OR_5$ in which $R_5$ is hydrogen, acyl or optionally substituted carbamoyl,
A is oxygen atom or sulfur atom, E is oxygen atom or methylene, and
G is lower alkylene, provided that when A is sulfur atom, E is methylene, and salts thereof exhibit serotonin $S_2$ receptor blocking activity, actions to relieve cerebral vasospasm and antithrombotic activity, and are of value as a prophylactic and therapeutic agent for ischemic cardiopathies, thrombosis, hypertension and cerebral circulatory disorders.

15 Claims, No Drawings

2-(PIPERAZINYLALKYL)-1-BENZOTHIEPIN, 1-BENZOXEPIN, AND 1,5-BENZODIOXEPIN DERIVATIVES

TECHNOLOGICAL FIELD

This invention relates to novel condensed seven-membered heterocyclic compounds useful as drugs, their production and use.

BACKGROUND OF THE ART

As the result of our intensive research on production of compounds which block the specific serotonin $S_2$-receptor, the inventors have succeeded in production of novel condensed seven-membered heterocyclic compounds which have excellent serotonin $S_2$-receptor blocking activity, activity to relieve cerebral vasospasm and antithrombotic activity, and are useful for prevention or treatment of ischemic cardiopathies such as angina pectoris and myocardial infarction, thrombosis, hypertension, and cerebral circulatory disorders such as cerebral vasospasm and transient ischemic attack, and completed the invention.

DETAILED DESCRIPTION OF THE INVENTION

This invention provides a compound of the formula:

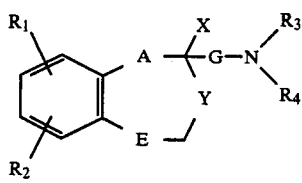

[wherein $R_1$ and $R_2$ are independently hydrogen, halogen, hydroxy, lower alkyl or lower alkoxy; $R_3$ and $R_4$ are independently hydrogen, or lower alkyl, cycloalkyl or aralkyl which may be substituted, or form, together with the adjacent nitrogen atom, a ring which may be substituted; X is hydrogen, lower alkyl which may be substituted, aryl which may be substituted, or carboxyl group which may be esterified or amidated; Y is $>C=O$ or $>CH-OR_5$ (where $R_5$ is hydrogen, acyl, or carbamoyl which may be substituted); A is oxygen atom or sulfur atom; E is oxygen atom or methylene; G is lower alkylene; provided that when A is sulfur atom, E is methylene], or a salt thereof.

In the above formula (I), halogen represented by $R_1$ or $R_2$ includes, for example, fluorine, chlorine, bromine, and iodine.

The lower alkyl group represented by $R_1$ or $R_2$ includes alkyl groups having about 1 to about 4 carbon atoms such as methyl, ethyl, propyl, isopropyl, butyl, sec-butyl, and tert-butyl; the lower alkoxy group represented by $R_1$ or $R_2$ includes alkoxy groups having about 1 to about 4 carbon atoms such as methoxy, ethoxy, propoxy, isopropoxy, butoxy, isobutoxy, sec-butoxy, and tert-butoxy. It is desirable that both of $R_1$ and $R_2$ are hydrogen or one of them is hydrogen and the other is lower alkoxy, and when one of $R_1$ and $R_2$ is lower alkoxy, the said alkoxy group is desirably bound to the para-position of E (the meta-position of A).

The lower alkyl group represented by $R_3$ or $R_4$ includes alkyl groups having about 1 to about 4 carbon atoms such as methyl, ethyl, propyl, isopropyl, butyl, isobutyl, sec-butyl, and tert-butyl, and the said alkyl groups may be substituted, for example, by $C_{3-8}$ cycloalkyl (e.g. cyclopropyl, cyclobutyl, cyclopentyl, cyclohexyl, cycloheptyl, cyclooctyl), halogen (e.g. fluorine, chlorine, bromine), hydroxy, lower ($C_{1-4}$) alkoxy (e.g. methoxy, ethoxy, propoxy, butoxy), lower ($C_{1-5}$) alkanoyloxy (e.g. acetoxy, propionyloxy, butyryloxy, pivaloyloxy), mono- or di-lower ($C_{1-4}$) alkylamino (e.g. methylamino, dimethylamino, methylethylamino), $C_{3-8}$ cycloalkylamino (e.g. cyclopentylamino, cyclohexylamino), lower ($C_{1-5}$) alkanoylamino (e.g. acetamido, propionamido), benzamido, lower ($C_{1-4}$) alkylthio (e.g. methylthio, ethylthio, propylthio, butylthio), carbamoyl, N-lower ($C_{1-4}$) alkylcarbamoyl (e.g. methylcarbamoyl, ethylcarbamoyl), or N,N-di-lower ($C_{1-4}$) alkylcarbamoyl (e.g. dimethylcarbamoyl, diethylcarbamoyl, methylethylcarbamoyl).

The cycloalkyl group represented by $R_3$ or $R_4$ includes cycloalkyl groups having about 3 to about 8 carbon atoms such as cyclopropyl, cyclobutyl, cyclopentyl, cyclohexyl, cycloheptyl and cyclooctyl, and the said cycloalkyl groups may be substituted by lower ($C_{1-4}$) alkyl (e.g. methyl, ethyl, propyl, butyl), lower ($C_{1-4}$) alkoxy (e.g. methoxy, ethoxy, propoxy, isopropoxy, butoxy), lower ($C_{1-5}$) alkanoylamino (e.g. acetamido), or hydroxy.

The aralkyl group represented by $R_3$ or $R_4$ includes phenyl-lower ($C_{1-4}$) alkyl groups such as benzyl, phenethyl, 3-phenylpropyl, α-methylbenzyl, α-ethylbenzyl, α-methylphenethyl, β-methylphenethyl, and β-ethylphenethyl, and the phenyl group in the said phenyl-lower alkyl groups may be substituted by one to three members of, for example, halogen (e.g. fluorine, chlorine, bromine, iodine), lower ($C_{1-4}$) alkyl (e.g. methyl, ethyl, propyl, butyl), lower ($C_{1-4}$) alkoxy (e.g. methoxy, ethoxy, propoxy, isopropoxy, butoxy), methylenedioxy, amino, nitro, or hydroxy. Such substituted phenyl-lower alkyl groups include, for example, 2-(4-chlorophenyl)ethyl, 2-(4-hydroxyphenyl)ethyl, 2-(4-methoxyphenyl)ethyl, 2-(3,4-dimethoxyphenyl)ethyl, 2-(3,4,5-trimethoxyphenyl)ethyl, 2-(3,4-methylenedioxyphenyl)ethyl, 2-(p-tolyl)ethyl, 3,4-dimethoxybenzyl, 3,4-methylenedioxybenzyl, 3,4,5-trimethoxybenzyl, 4-ethylbenzyl, and 4-chlorobenzyl.

The ring formed by $R_3$ and $R_4$ together with the adjacent nitrogen atom includes cyclic amino groups which may contain a hetero atom such as nitrogen, oxygen or sulfur in addition to the said nitrogen atom, for example, 5- to 7-membered cyclic amino groups such as pyrrolidinyl, morpholinyl, piperidyl, piperazinyl, and homopiperazinyl. The said cyclic amino groups may have a substituent or substituents at the positions where substitution may occur, and such a substituent includes lower ($C_{1-4}$) alkyl (e.g. methyl, ethyl, propyl, butyl), aryl, aralkyl, acyl, and hetero-rings. The aryl group as the substituent includes, for example, phenyl group which may be substituted by one to three members of, for example, halogen (e.g. fluorine, chlorine, bromine, iodine), lower ($C_{1-4}$) alkyl (e.g. methyl, ethyl, propyl, butyl), lower ($C_{1-4}$) alkoxy (e.g. methoxy, ethoxy, propoxy, isopropoxy, butoxy), methylenedioxy, amino, nitro, or hydroxy. The aralkyl group as the substituent includes, for example, phenyl-lower($C_{1-4}$) alkyl groups such as benzyl and phenethyl, diphenyl-lower($C_{1-4}$) alkyl groups such as benzhydryl and triphenyl-lower($C_{1-4}$) alkyl. The acyl group as the substituent includes, for example, lower($C_{1-4}$) aliphatic acid residues such as lower($C_{1-4}$) alkanoyl (e.g. acetyl, propionyl, butyryl), and aromatic organic acid residues such as benzoyl, phenyl-lower($C_{1-4}$) alkanoyl, and phenyl-lower($C_{1-4}$) alkenoyl (e.g. cinnamoyl). The phenyl groups in the said aralkyl groups and aromatic organic acid residues may be substituted by one to three members of, for example, halogen (e.g. fluorine, chlorine, bromine, iodine), lower ($C_{1-4}$) alkyl (e.g. methyl, ethyl, propyl, butyl), lower ($C_{1-4}$) alkoxy (e.g. methoxy, ethoxy, propoxy, isopropoxy, butoxy), methylenedioxy, amino, nitro, or hydroxy. The hetero ring as the substituent includes, for example, 5- to 7-membered rings containing 1 to 3 nitrogen atoms, such as pyrrolyl, pyrazolyl, imidazolyl, pyridyl, pyrimidinyl, pyridazinyl, triazinyl, and azepinyl.

It is desirable that $R_3$ and $R_4$ together with the adjacent nitrogen atom form a ring substituted by an aryl group, and aryl-substituted piperazinyl is more desirable.

The lower alkyl group represented by X includes alkyl groups having about 1 to 4 carbon atoms such as methyl, ethyl, propyl, isopropyl, butyl, isobutyl, sec-butyl, and tert-butyl, and these groups may be substituted by, for example, oxo, hydroxy, acyloxy, or aryl. The lower alkyl group substituted by oxo includes, for example, lower ($C_{1-4}$) alkanoyl groups such as acetyl, propionyl and butyryl. The lower alkyl group substituted by hydroxy includes, for example, hydroxymethyl. Acyl group as acyloxy groups includes acyl groups derived from lower fatty acids such as lower ($C_{1-5}$) alkanoyl (e.g. acetyl, propionyl, butyryl), and the lower alkyl group substituted by the said acyloxy group includes, for example, acetyloxymethyl, propionyloxymethyl, and butyryloxymethyl. The lower alkyl group substituted by aryl group includes lower($C_{1-4}$) alkyl groups substituted by phenyl group such as benzyl, and the said phenyl group may be substituted with one to three members of, for example, halogen (e.g. fluorine, chlorine, bromine, iodine), lower($C_{1-4}$) alkyl (e.g. methyl, ethyl, propyl, butyl), lower($C_{1-4}$) alkoxy (e.g. methoxy, ethoxy, propoxy, isopropoxy, butoxy), methylenedioxy, amino, nitro, or hydroxy.

The aryl group represented by X includes, for example, phenyl group, and the said phenyl group may be substituted with one to three members of, for example, halogen (e.g. fluorine, chlorine, bromine, iodine), lower ($C_{1-4}$) alkyl (e.g. methyl, ethyl, propyl, butyl), lower ($C_{1-4}$) alkoxy (e.g. methoxy, ethoxy, propoxy, isopropoxy, butoxy), methylenedioxy, amino, nitro, or hydroxy.

The esterified carboxyl group represented by X includes, for example, lower ($C_{1-4}$) alkoxycarbonyl such as methoxycarbonyl, ethoxycarbonyl, propoxycarbonyl, isopropoxycarbonyl, butoxycarbonyl, isobutoxycarbonyl, sec-butoxycarbonyl, and tert-butoxycarbonyl, and phenyl-lower ($C_{1-4}$) alkoxycarbonyl such as benzyloxycarbonyl.

The amidated carboxyl group represented by X includes, for example, carbamoyl group, and the amino group in the said carbamoyl group may be substituted by one or two members of lower($C_{1-4}$) alkyl, phenyl, phenyl-lower ($C_{1-4}$) alkyl, and the like. An esterified carboxyl group is desirable as X, and lower alkoxycarbonyl group is more desirable.

The acyl group represented by $R_5$ includes, for example, alkanoyl groups having about 1 to 6 carbon atoms such as acetyl, propionyl, butyryl, valeryl, and pivaloyl, and acyl groups including phenyl-lower($C_{1-6}$) alkanoyl derived from aromatic carboxylic acid, such as benzoyl, phenylacetyl, and phenylpropionyl, and when the aromatic ring in the said aromatic carboxylic acid is a phenyl group, the said phenyl group may be substituted by one to three members of, for example, halogen (e.g. fluorine, chlorine, bromine, iodine), lower($C_{1-4}$) alkyl (e.g. methyl, ethyl, propyl, butyl), lower($C_{1-4}$) alkoxy (e.g. methoxy, ethoxy, propoxy, isopropoxy, butoxy), methylenedioxy, amino, nitro, or hydroxy.

The carbamoyl group which may be substituted, represented by $R_5$ includes, for example, a carbamoyl group substituted by lower($C_{1-4}$) alkyl (e.g. methyl, ethyl, propyl, butyl), phenyl, or phenyl-lower ($C_{1-4}$) alkyl (e.g. benzyl, phenethyl). The said phenyl group or the phenyl group in the phenyl-lower alkyl group may be substituted by one to three members of, for example, halogen (e.g. fluorine, chlorine, bromine, iodine), lower ($C_{1-4}$) alkyl (e.g. methyl, ethyl, propyl, butyl), lower ($C_{1-4}$) alkoxy (e.g. methoxy, ethoxy, propoxy, isopropoxy, butoxy), methylenedioxy, amino, nitro, or hydroxy. Y is desirably hydroxymethylene.

When A is sulfur atom, sulfide, sulfoxide or sulfone is formed according to the state of oxidation, and sulfide is the most desirable.

The lower alkylene group represented by G includes, for example, alkylene groups having about 1 to about 6 carbon atoms such as methylene, ethylene, trimethylene, tetramethylene, pentamethylene and hexamethylene. Among them, ethylene, trimethylene, tetramethylene, and pentamethylene are preferable, trimethylene being the most desirable. The salt of the compound (I) includes, for example, inorganic acid salts such as hydrochloride, hydrobromide, sulfate, nitrate, and phosphate, and organic acid salts such as acetate, tartrate, citrate, fumarate, maleate, toluenesulfonate, and methanesulfonate, which are pharmaceutically acceptable. Among the compounds (I), the compounds having the following formula and their pharmaceutically acceptable salts are desirable:

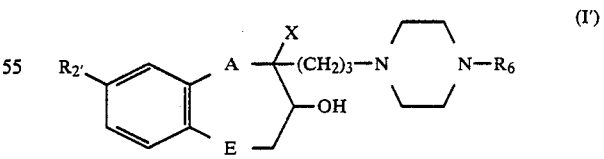

[wherein $R_6$ is a phenyl group which may be substituted by one to three members of halogen, lower($C_{1-4}$) alkyl, lower ($C_{1-4}$) alkoxy, methylenedioxy, amino, nitro or hydroxy; $R_{2'}$ is hydrogen or lower($C_{1-4}$) alkoxy; X is lower ($C_{1-4}$) alkoxycarbonyl group; A and E mean the same as described above].

Compounds in this invention include, for example, the compounds shown in Table 1.

TABLE 1

Structure:

$R_1$ at position (a), (b) positions on aromatic ring; $R_2$ at position (d); ring connected to A—C(X)(Y)—G—N(R_3)(R_4); E—CH_2 forms fused ring.

| R₁ (binding site) | R₂ (binding site) | —N(R₃)(R₄) | X | Y | A | E | G |
|---|---|---|---|---|---|---|---|
| H | —OCH₃ (b) | 4-phenyl-piperazin-1-yl | —COOCH₃ | CH—OH | S | CH₂ | —(CH₂)₃— |
| H | —OCH₃ (b) | 4-(4-fluorophenyl)-piperazin-1-yl | —COOCH₃ | CH—OH | S | CH₂ | —(CH₂)₃— |
| H | H | 4-(pyridin-2-yl)-piperazin-1-yl | —COOCH₃ | CH—OH | S | CH₂ | —(CH₂)₃— |
| H | —OCH₃ (b) | 4-phenyl-piperidin-1-yl | —COOCH₃ | CH—OH | S | CH₂ | —(CH₂)₃— |
| H | —OCH₃ (b) | 4-phenyl-piperazin-1-yl | —COOCH₃ | CH—OH | O | CH₂ | —(CH₂)₃— |
| H | H | 4-(4-fluorobenzoyl)-piperidin-1-yl | —COOCH₃ | CH—OH | O | CH₂ | —(CH₂)₃— |
| H | —OCH₃ (b) | 4-(4-fluorobenzoyl)-piperidin-1-yl | —COOCH₃ | CH—OH | S | CH₂ | —(CH₂)₃— |
| H | Cl (b) | 4-phenyl-piperazin-1-yl | —COOCH₃ | CH—OH | O | CH₂ | —(CH₂)₃— |
| H | Cl (b) | 4-phenyl-piperidin-1-yl | —COOCH₃ | CH—OH | O | CH₂ | —(CH₂)₃— |
| H | Cl (b) | 4-(4-fluorophenyl)-piperazin-1-yl | —COOCH₃ | CH—OH | O | CH₂ | —(CH₂)₃— |
| H | Cl (b) | 4-(pyridin-2-yl)-piperazin-1-yl | —COOCH₃ | CH—OH | O | CH₂ | —(CH₂)₃— |

TABLE 1-continued $$\underset{R_2}{\overset{R_1}{\bigcirc}}\overset{(a)}{\underset{(d)}{(b)}}\overset{A}{\underset{E}{\bigg\langle}}\overset{X}{\underset{Y}{\bigg\rangle}}G-N\overset{R_3}{\underset{R_4}{\bigg\langle}}$$

| R₁ (binding site) | R₂ (binding site) | $-N\begin{smallmatrix}R_3\\R_4\end{smallmatrix}$ | X | Y | A | E | G |
|---|---|---|---|---|---|---|---|
| H | Cl (b) | piperazinyl-(2-methoxyphenyl) | —COOCH₃ | CH—OH | O | CH₂ | —(CH₂)₃— |
| H | Cl (c) | piperazinyl-phenyl | —COOCH₃ | CH—OH | O | CH₂ | —(CH₂)₃— |
| H | H | piperazinyl-(4-fluorophenyl) | —COOCH₃ | CH—OH | O | O | —(CH₂)₃— |
| H | H | piperazinyl-(2-pyridyl) | —COOCH₃ | CH—OH | O | CH₂ | —(CH₂)₃— |
| H | —OCH₃ (b) | piperazinyl-phenyl | —COOCH₃ | CH—OH | O | CH₂ | —(CH₂)₃— |
| H | —OCH₃ (b) | piperazinyl-phenyl | —COOCH₃ | CH—OH | O | O | —(CH₂)₃— |
| H | —OCH₃ (b) | piperidinyl-C(O)-(4-fluorophenyl) | —COOCH₃ | CH—OH | S | CH₂ | —(CH₂)₃— |
| H | —OCH₃ (b) | piperazinyl-(2-methoxyphenyl) | —COOCH₃ | CH—OH | S | CH₂ | —(CH₂)₃— |
| H | —OCH₃ (b) | —N(CH₃)—(CH₂)₂—(3,4-dimethoxyphenyl) | —COOCH₃ | CH—OH | S | CH₂ | —(CH₂)₃— |
| H | —OCH₃ (b) | —N(CH₃)—(CH₂)₂—phenyl | —COOCH₃ | CH—OH | S | CH₂ | —(CH₂)₃— |

TABLE 1-continued

Structure:
R₁ at position (a) or (b); R₂ at position (c) or (d) on benzene ring bearing A-G-N(R₃)(R₄) with X substituent, and E-Y branch.

| R₁ (binding site) | R₂ (binding site) | -N(R₃)(R₄) | X | Y | A | E | G |
|---|---|---|---|---|---|---|---|
| H | —OCH₃ (b) | —N(CH₂-C₆H₅)—(CH₂)₃ (N-methyl, N-(3-phenylpropyl)) | —COOCH₃ | CH—OH | S | CH₂ | —(CH₂)₃— |
| H | —CH₃ (b) | 4-phenylpiperazin-1-yl | —COOCH₃ | CH—OH | O | CH₂ | —(CH₂)₃— |
| H | —CH₃ (c) | 4-phenylpiperazin-1-yl | —COOCH₃ | CH—OH | O | CH₂ | —(CH₂)₃— |
| H | Cl (b) | —N(CH₃)—(CH₂)₃—C₆H₄-4-Cl | —COOCH₃ | CH—OH | O | CH₂ | —(CH₂)₃— |
| H | Cl (b) | —N(CH₃)—(CH₂)₂—(3,4-dimethoxyphenyl) | —COOCH₃ | CH—OH | O | CH₂ | —(CH₂)₃— |
| H | Cl (c) | —N(CH₃)—(CH₂)₂—(3,4-dimethoxyphenyl) | —COOCH₃ | CH—OH | O | CH₂ | —(CH₂)₃— |
| H | —OCH₃ (c) | —N(CH₃)—(CH₂)₂—(3,4-dimethoxyphenyl) | —COOCH₃ | CH—OH | O | CH₂ | —(CH₂)₃— |
| H | —OC₂H₅ (b) | 4-phenylpiperazin-1-yl | —COOCH₃ | CH—OH | S | CH₂ | —(CH₂)₃— |
| H | —OC₂H₅ (b) | 4-(4-fluorophenyl)piperazin-1-yl | —COOCH₃ | CH—OH | O | CH₂ | —(CH₂)₃— |
| H | —OCH₃ (b) | 4-(4-fluorophenyl)piperazin-1-yl | —COOC₂H₅ | CH—OH | O | CH₂ | —(CH₂)₃— |

TABLE 1-continued

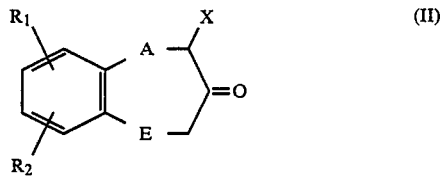

| $R_1$ (binding site) | $R_2$ (binding site) | $-N\begin{smallmatrix}R_3\\R_4\end{smallmatrix}$ | X | Y | A | E | G |
|---|---|---|---|---|---|---|---|
| H | —OCH$_3$ (b) |  | —COOCH$_3$ | $\begin{smallmatrix}\diagdown\\CHOCOCH_3\\\diagup\end{smallmatrix}$ | S | CH$_2$ | —(CH$_2$)$_3$— |

The compound (I) of this invention can be produced, for example, by condensation, by condensation followed by reduction, or by condensation followed by reduction and then acylation or carbamoylation, of a compound having the formula:

$$\text{(II)}$$

[wherein the symbols mean the same as described above] and a compound having the formula:

$$W-G-N\begin{smallmatrix}R_3\\R_4\end{smallmatrix} \quad \text{(III)}$$

[where G, R$_3$ and R$_4$ mean the same as described above; W means halogen or a group represented by the formula: R—SO$_2$—O— (where R is lower (C$_{1-4}$) alkyl, phenyl, or p-tolyl)].

The said condensation is usually carried out in the presence of a base. Such a base includes, for example, inorganic bases such as potassium carbonate, potassium hydrogen carbonate, sodium carbonate, sodium methoxide, sodium hydride, and lithium diisopropylamide, and organic amines such as triethylamine, pyridine, and 1,8-diazabicyclo[5,4,0]-7-undecene. The reaction is allowed to proceed advantageously by using, for example, sodium iodide, or potassium iodide as a catalyst. The reaction described above is carried out usually in an organic solvent (e.g. acetone, 2-butanone, acetonitrile, N,N-dimethylformamide, methylene chloride, benzene, toluene, tetrahydrofuran, dioxane) at −20° to +150° C., preferably at about +20° to about +120° C.

Reduction of the compound wherein Y is >C═O in the formula (I) obtained by the condensation is carried out, for example, by reduction with metal hydride such as lithium aluminum hydride, lithium borohydride, lithium cyanoborohydride, sodium borohydride, sodium cyanoborohydride or lithium aluminum tri-tert-butoxyhydride, by reduction with metallic sodium or metallic magnesium and an alcohol, by catalytic reduction with metal such as platinum, palladium, rhodium, or a mixture thereof with an arbitrary carrier, by reduction with metal such as iron or zinc and an acid such as hydrochloric acid or acetic acid, by electrolytic reduction, by reduction with a reducing enzyme, or by reduction with boron hydride such as diborane or a complex of boron hydride with amine such as borane-trimethylamine. The reaction described above is usually carried out in the presence of water or an organic solvent (e.g. methanol, ethanol, ethylether, dioxane, methylene chloride, chloroform, benzene, toluene, acetic acid, dimethylformamide, dimethylacetamide), and the reaction temperature varies according to the means of reduction but is preferable about −20° to about +100° C. Acylation and carbamoylation after condensation-reduction are carried out by using usual methods of acylation or carbamoylation of alcohol derivatives. Such means of acylation include, for example, the reaction of a reactive derivative of an organic acid corresponding to R$_5$ (acid anhydride, acid halide, etc.) in the presence of an organic base such as pyridine, triethylamine, or N,N,-dimethylaniline, or an inorganic base such as sodium carbonate, potassium carbonate or sodium hydrogen carbonate. The reaction described above is usually carried out in an organic solvent (e.g. methanol, ethanol, ethylether, dioxane, methylene chloride, toluene, dimethylformamide, pyridine), and the reaction temperature is preferably about −20° to about +100° C. Carbamoylation is carried out, for example, by the reaction of the alcohol derivative obtained by the reduction, with an isocyanate corresponding to R$_5$ (e.g. methyl isocyanate, ethyl isocyanate, phenyl isocyanate, p-chlorophenyl isocyanate). This reaction is usually carried out in an appropriate organic solvent (e.g. methanol, ethanol, acetonitrile, dioxane, tetrahydrofuran, methylenechloride, chloroform, toluene, N,N-dimethylformamide), and the reaction temperature is preferably about −20° to about +150° C.

The compound (I) of this invention can also be produced, for example, by reacting a compound having the formula:

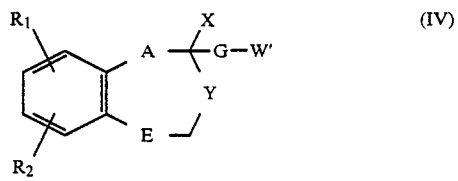

[wherein W' is halogen or a group represented by the formula: R'—SO₂—O— (wherein R' is a lower(C₁₋₄) alkyl, phenyl or p-tolyl), and other symbols are the same as described above] with an amine having the formula:

[where R₃ and R₄ are the same as described above]. The reaction of a compound (IV) with an amine (V) is carried out in an appropriate organic solvent (e.g. methanol, ethanol, dioxane, acetonitrile, tetrahydrofuran, N,N-dimethylformamide, methylene chloride, dimethyl sulfoxide, and an arbitrary mixture thereof). The reaction temperature is preferably about 0° C. to about +150° C., and an organic base such as triethylamine, pyridine, or N,N-dimethylaniline, or an inorganic base such as potassium carbonate, sodium carbonate or sodium hydrogen carbonate may be used as a catalyst to promote the reaction.

After the reaction, the compound wherein Y is >C=O in the formula (I) is subjected to the reduction described above or to the reduction followed by acylation or by carbamoylation, to give the compound wherein Y is >CH—OR₅ in the formula (I). The compound of this invention (I) can also be produced by condensation under reductive conditions, of a compound having the formula:

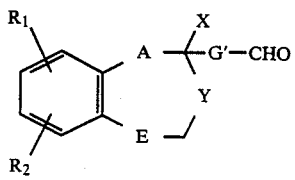

[where G' is an alkylene group which is smaller than the lower alkylenen group represented by G by an methylene group, and other symbols are the same as described before] with a compound (V).

The said reductive conditions include, for example, the reaction conditions of catalytic reduction using metal such as platinum, palladium, Raney nickel, or rhodium or a mixture thereof with an arbitrary carrier, of reduction with metal hydride such as lithium aluminum hydride, lithium borohydride, lithium cyanoborohydride, sodium borohydride, or sodium caynoborohydride, of reduction with metallic sodium or metallic magnesium with an alcohol, of reduction with metal such as iron or zinc with an acid such as hydrochloric acid or acetic acid, of electrolytic reduction, and of reduction with a reducing enzyme. These reactions are usually carried out in the presence of water or an organic solvent (e.g. methanol, ethanol, ethylether, dioxane, methylene chloride, chloroform, benzene, toluene, acetic acid, dimethylformamide, dimethylacetamide) and the reaction temperature varies according to the means of reduction but is preferably about −20° to about +100° C. This reaction can proceed satisfactorily under atmospheric pressure, but may be carried out under elevated or reduced pressure according to the circumstances.

The compound (I) of this invention can also be produced, for example, by reduction of the amido group in a compound having the formula:

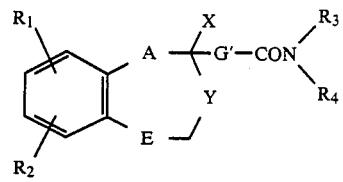

[wherein the symbols are the same as described above]. The said reduction may be carried out by using, for example, lithium aluminum hydride, sodium dihydrobis[2-methoxyethoxy]alminate, sodium acetoxyborohydride, aluminum hydride, diborane, or alkylborane. The reaction is usually carried out in the presence of an organic solvent (e.g. ethylether, tetrahydrofuran, dioxane, toluene, benzene), and the reaction temperature varies according to the means of reduction, but is preferably about −20° to about +120° C. In the reduction, when X is, for example, an esterified or amidated carboxyl group and Y is >C=O in the formula (VII), these functional groups can be reduced simultaneously, or only the desired amido group can be reduced by protecting the carbonyl group or by selecting an appropriate reducing agent if necessary.

The compound wherein A is sulfoxide or sulfone in the formula (I) can also be produced by oxidation of the corresponding sulfide. The said oxidation is carried out, for example, by reaction with an organic peracid (e.g. m-chloroperbenzoic acid, peracetic acid) or an inorganic oxidant (e.g. hydrogen peroxide, periodic acid). The reaction is usually carried out in the presence of water or an organic solvent (e.g. methanol, ethanol, dioxane, dichloromethane) usually at −20° to +100° C.

The desired compound (I) of this invention thus obtained can be isolated by usual methods of isolation and purification, such as extraction, concentration, neutralization, filtration, recrystallization, column chromatography, and thin layer chromatography. When Y in the formula (I) is, for example, >CH—OR₅, there are at least two stereoisomers. Each of these isomers and mixtures thereof are of course included in the scope of this invention, and if necessary, each of the isomers can be produced separately. For example, by the above reactions using a single isomer of the starting material (IV) or (VI), the single optical isomer can be produced, and when the product is a mixture of two or more isomers, the mixture can be separated into the respective isomers by usual methods of separation, for example, by formation of a salt with an optically active acid (e.g. camphor sulfonic acid, tartaric acid, dibenzoyl tartaric acid, malic acid) or by various chromatographic methods, or by fractional recrystallization.

The starting compounds (II), (IV), (VI), and (VII) can be produced, for example, by the methods shown in the following reaction schema:

(i) Compounds (II)

(a) When X is an aryl which may be substituted, or a carboxyl which may be esterified or amidated.

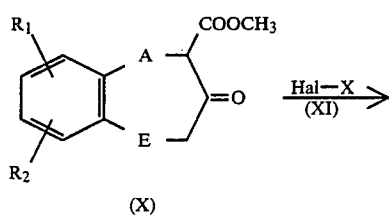
(VIII) → (IX)
(b) When X is an alkyl group which may be substituted.
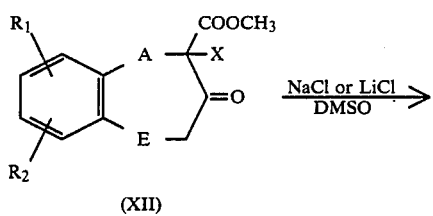
(X) →[Hal—X (XI)] 
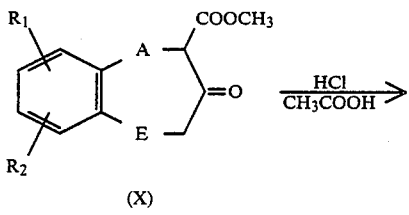
(XII) →[NaCl or LiCl / DMSO]
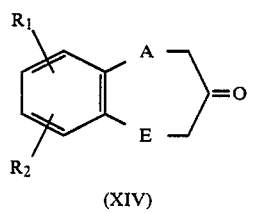
(XIII)
(c) When X is hydrogen.
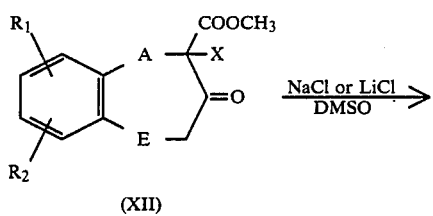
(X) →[HCl / CH₃COOH]
(XIV)
(ii) Compound (IV)
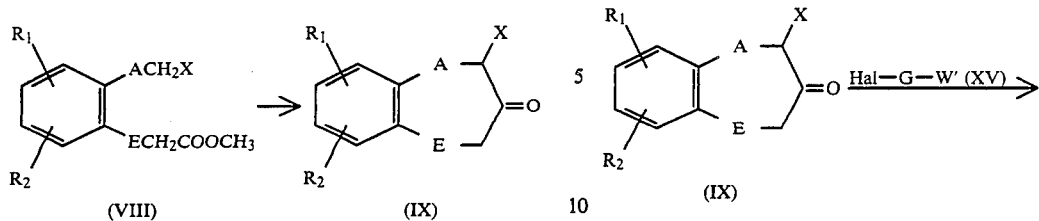
(IX) →[Hal—G—W' (XV)]
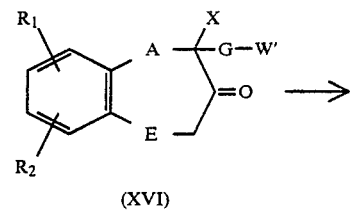
(XVI) →
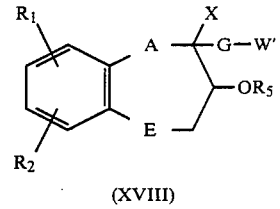
(XVII) →
(XVIII)
(iii) Compound (VI)
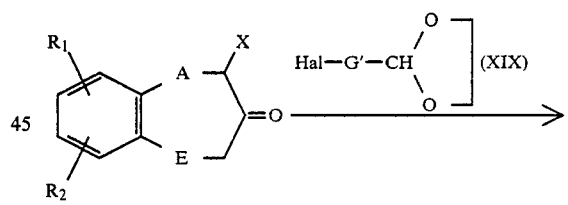
(IX) →[Hal—G'—CH(O)(O) (XIX)]
(XX) →[H⁺]
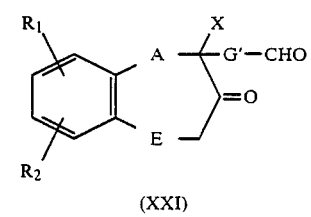
(XXI)

-continued

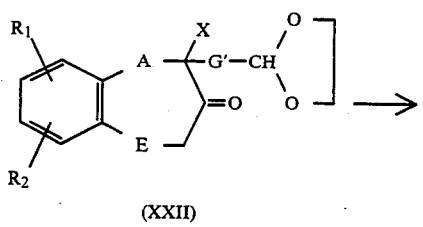

(XXII)

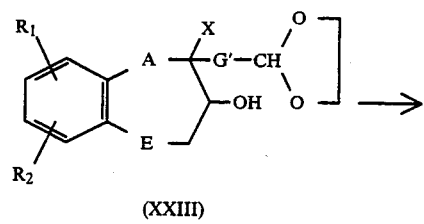

(XXIII)

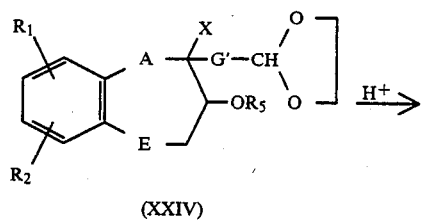

(XXIV)

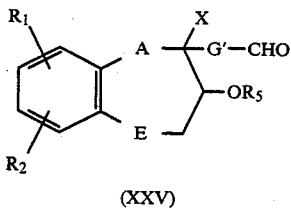

(XXV)

(iv) Compound (VII)

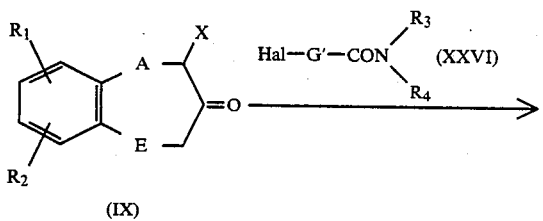

(IX)

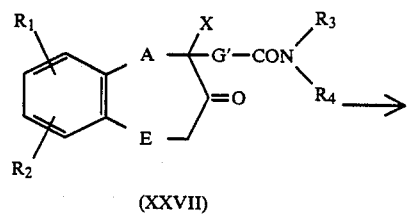

(XXVII)

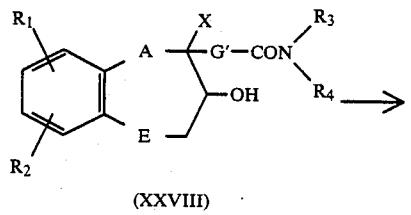

(XXVIII)

-continued

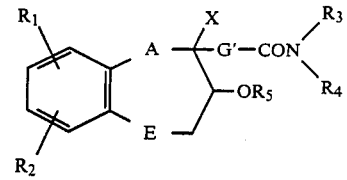

(XXIX)

In the reaction schema described above, Hal is halogen (e.g. bromine, chlorine) and the other symbols are the same as described before.

The ring-closure reaction to produce a compound (IX) from a compound (VIII) is usually carried out in an organic solvent (e.g. toluene, xylene), and proceeds advantageously in the presence of a base (e.g. sodium methoxide, sodium ethoxide, potassium tert-butoxide, sodium hydride). The preferable reaction temperature is usually about $+20°$ to about $+200°$ C. When the compound (IX) is obtained as an alkali metal salt thereof, the compound (IX) can be isolated by usual methods after neutralization with acetic acid, hydrochloric acid, or sulfuric acid.

When X is lower alkyl which may be substituted in the formula (II), the compound (XIII) can be obtained by elimination of the ester group after alkylation of the compound (X) obtained by the methods (i)-(a) described above.

The reaction of the compound (X) with the compound (XI) can be carried out in the presence of a base (e.g. sodium carbonate, potassium carbonate, sodium hydrogen carbonate, sodium hydride, sodium methoxide, triethylamine, pyridine) in an appropriate organic solvent (e.g. acetone, 2-butanone, acetonitrile, N,N-dimethylformamide, dimethylsulfoxide, benzene, toluene, tetrahydrofuran). The reaction can be carried out smoothly by addition of an iodide such as potassium iodide or sodium iodide. The reaction temperature is preferably about $-20°$ to about $+150°$ C.

The reaction (XII)→(XIII) is carried out, according to a usual elimination method of ester group, by heating the compound (XII) at about $+50°$ to about $+160°$ C. in the presence of a salt (e.g. sodium chloride, lithium chloride, calcium chloride, sodium bromide) in an appropriate organic solvent (e.g. dimethyl sulfoxide, N,N-dimethylformamide, N,N-dimethylacetamide).

When X in the formula (II) is hydrogen, the compound (XIV) can be obtained by subjecting the compound (X) to a reaction similar to the reaction (XII)→(XIII).

The reaction of the compound (IX) with the compound (XV) can be carried out similarly to the reaction of the compound (X) with the compound (XI). The compound (XVII) can be obtained by the reduction of the compound (XVI). The said reduction may be carried out by the reduction with a metal hydride such as lithium aluminum hydride, lithium borohydride, lithium cyanoborohydride, sodium borohydride, sodium cyanoborohydride, or lithium aluminum tri-tert-butoxyhydride, by reduction with metallic sodium or metallic magnesium with an alcohol, by catalytic reduction using metal such as platinum, palladium or rhodium, or a mixture thereof with an arbitrary carrier as a catalyst, by reduction with a metal such as iron or zinc with an acid such as hydrochloric acid or acetic acid, by electrolytic reduction, by reduction with a reducing enzyme, or by reduction with a boron hydride such as diborane or with a complex of a boron hydride with an amine such as boranetrimethylamine. The reaction is usually carried out in the presence of water or an organic solvent (e.g. methanol, ethanol, ethylether, dioxane, methylene chloride, chloroform, benzene, toluene, acetic acid, dimethylformamide, dimethylacetamide), and the reaction temperature varies according to the means of reduction but is preferably about $-20°$ to about $+100°$ C.

The reaction (XVII)→(XVIII) can be carried out by a usual method of acylation or carbamoylation of alcohol derivatives. The method of the said acylation includes, for example, the reaction of a reactive derivative of an organic acid corresponding to $R_5$ (e.g. acid anhydride, acid halide) with the compound (XVII) in the presence of an organic base (e.g. pyridine, triethylamine, N,N-dimethylaniline) or an inorganic base (e.g. sodium carbonate, potassium carbonate, sodium hydrogen carbonate).

The reaction described above is usually carried out in an organic solvent (e.g. ethylether, dioxane, methylene chloride, toluene, dimethylformamide, pyridine), and the reaction temperature is preferably about $-20°$ to about $+100°$ C. Carbamoylation can be carried out for example by the reaction of the alcohol derivative (XVII) obtained by reduction, with an isocyanate corresponding to $R_5$ (e.g. methyl isocyanate, ethyl isocyanate, phenyl isocyanate, p-chlorophenyl isocyanate). The reaction is usually carried out in an appropriate organic solvent (e.g. acetonitrile, dioxane, tetrahydrofuran, methylene chloride, chloroform, toluene, N,N-dimethylformamide), and the reaction temperature is preferably about $-20°$ to about $+150°$ C.

The reaction of the compound (IX) with the compound (XIX) can be carried out similarly to the reaction of the compound (X) with the compound (XI). The compound (XXI) can be obtained by hydrolyzing the compound (XX) with a diluted mineral acid (e.g. hydrochloric acid, sulfuric acid). The compound (XXIII) can be obtained by subjecting the compound (XXII) to a reaction similar to the reduction (XVI)→(XVII). The reaction (XXIII)→(XXIV) can be carried out similarly to the reaction (XVII)→(XVIII). The compound (XXV) can be obtained by subjecting the compound (XXIV) to a reaction similar to the reaction (XX)→(XXI).

The reaction of the compound (IX) with the compound (XXVI) can be carried out similarly to the reaction of the compound (X) with the compound (XI).

The reaction (XXVII)→(XXVIII), and the reaction (XXVIII)→(XXIX) can be carried out similarly to the reaction (XVI)→(XVII), and to the reaction (XVII)→(XVIII), respectively.

In the process for production of the compound (I) and intermediates thereof described above, the compounds used in the reactions may, as far as they do not interfere with the reactions, be used in a form of inorganic acid salt such as hydrochloride, hydrobromide, sulfate, nitrate, or phosphate, or organic acid salt such as acetate, tartarate, citrate, fumalate, maleate, toluenesulfonate, or methanesulfonate, or metal salt such as sodium salt, potassium salt, calcium salt, or aluminum salt, or salt with a base such as triethylamine salt, guanidine salt, ammonium salt, hydrazine salt, quinine salt, or cinchonine salt.

This invention also provides the intermediate (IV) and a salt thereof which are useful for the production of the compound (I). W′ in the formula (IV) is desirably halogen.

Actions

The compounds of the invention, i.e. the compounds having the formula (I) and salts thereof have the specific serotonin $S_2$-receptor blocking activity, activity to relieve cerebral vasospasm and antithrombotic activity in animals particularly in mammals (e.g. human, pig, dog, cat, rabbit, guinea pig, rat), and are useful as drugs for prevention or treatment of ischemic cardiopathies such as angina pectoris and myocardial infarction, thrombosis, hypertension, and cerebral circulatory disorders such as cerebral vasospasm and transient ischemic attack. The compounds of this invention are of low toxicity, well absorbed even on oral administration, and highly stable, so that the compounds, when used as above-mentioned drugs, can be safely administered orally or parenterally, per se or in a pharmaceutical formulation such as powder, granule, tablet, capsule or injection in admixture with a suitable pharmaceutically acceptable carrier, excipient or diluent. While the dose varies depending upon the conditions of the disease to be treated and upon the administration route, in case of administration to human adult for the purpose of treatment of ischemic cardiopathies or hypertension, for example, the compounds may be desirably administered orally at a single dose of, normally about 0.1–10 mg/kg, preferably about 0.3–3 mg/kg, or intravenously at a single dose of about 0.003–0.1 mg/kg, preferably about 0.01–0.1 mg/kg, about once to about three times a day according to the conditions.

When the compounds (I) are administered for the purpose of treatment of cerebral circulatory disorders, for example, the compounds may be desirably administered orally at single dose of, normally about 0.1–50 mg/kg, preferably about 0.3–30 mg/kg, or intravenously at a single dose of about 0.003–10 mg/kg, preferably about 0.01–1 mg/kg, about once to about three times a day according to the conditions.

EXAMPLES

The invention is illustrated in more detail by Reference Examples, Examples and Preparation Example in the following, but the invention should not be limited thereto.

REFERENCE EXAMPLE 1

A mixture of 5.0 g of methyl 3-oxo-2,3,4,5-tetrahydro-1-benzoxepin-2-carboxylate, 7.1 g of 1-bromo-3-chloropropane, 1.5 g of potassium iodide, 6.3 g of potassium carbonate and 60 ml of acetonitrile is heated under refluxing for 4 hours. After cooling, the inorganic substances are filtered off and the filtrate is concentrated under reduced pressure. The residue is treated with water and then extracted with ethyl acetate. The organic layer is washed with water, dried, and evaporated under reduced pressure. The residue is purified by column chromatography on silica gel (eluant: hexane:ethyl acetate=8:1→2:1), to give 5.5 g of methyl 2-(3-chloropropyl)-3-oxo-2,3,4,5-tetrahydro-1-benzoxepin-2-carboxylate as a colorless oil. Recrystallization from ethanol gives 4.4 g of colorless prisms: m.p. 75°–77° C.

Elementary analysis for $C_{15}H_{17}ClO_4$: Calculated: C, 60.71; H, 5.77. Found: C, 60.51; H, 5.72.

REFERENCE EXAMPLE 2

To a suspension of 2.0 g of methyl 2-(3-chloropropyl)-3-oxo-2,3,4,5-tetrahydro-1-benzoxepin-2-carboxylate obtained in Reference Example 1 in 30 ml of methanol, sodium borohydride is added in small portions with stirring and under ice-cooling. After completion of the reaction, the reaction mixture is treated with water and extracted with ethyl acetate. The organic layer is washed with water, dried, and evaporated under reduced pressure. The residue is purified by column chromatography on silica gel (eluant: hexane:ethyl acetate=3:1→1:1). From the first fraction eluted, methyl 2-(3-chloropropyl)-3-hydroxy-2,3,4,5-tetrahydro-1-benzoxepin-2-carboxylate (A isomer) is obtained as a colorless oil. Mass spectrum m/e: 298, 300 (M+). IR $\nu_{max}^{neat}$ cm$^{-1}$: 3500 (OH), 1735. NMR(CDCl$_3$) δ: 2.0 (6H, multiplet), 3.0(2H, multiplet), 3.5 (2H, triplet, ClCH$_2$—), 3.70 (3H, s, OCH$_3$), 4.18 (1H, multiplet, C$_3$—H).

From the subsequent fraction eluted, 0.66 g of methyl 2-(3-chloropropyl)-3-hydroxy-2,3,4,5-tetrahydro-1-benzoxepin-2-carboxylate (B isomer) is obtained as crystals. Recrystallization from ethyl acetate-hexane gives colorless prisms: m.p. 107°–109° C.

Elementary analysis for C$_{15}$H$_{19}$ClO$_4$: Calculated: C, 60.30; H, 6.41. Found: C, 60.29; H, 6.49.

IR $\nu_{max}^{KBr}$ cm$^{-1}$: 3500 (OH), 1740.

REFERENCE EXAMPLE 3

To a mixture of 4.1 g of 60% sodium hydride in 150 ml of xylene is added 0.3 ml of tert-butanol, and a solution of 10 g of methyl 2-methoxycarbonylmethyloxyphenoxyacetate in 100 ml of xylene is added dropwise to the mixture at 140°–150° C. (for 8 hours). To the reaction mixture 7 g of acetic acid is added and the precipitates are filtered off. The filtrate is concentrated under reduced pressure, and the residue is purified by column chromatography on silica gel (eluant: hexane:ethyl acetate=3:1 2:1), to give 6.5 g of methyl 3-oxo-3,4-dihydro-2H-1,5-benzodioxepin-2-carboxylate as a colorless oil. Mass spectrum m/e: 222 (M+). IR $\nu_{max}^{neat}$ cm$^{-1}$: 1750. NMR (CDCl$_3$) δ: 3.75(3H, singlet, OCH$_3$), 4.68 (2H, double doublet, C$_4$—H), 5.32 (1H, singlet, C$_2$—H).

REFERENCE EXAMPLE 4

A mixture of 5.5 g of methyl 3-oxo-3,4-dihydro-2H-1,5-benzodioxepin-2-carboxylate obtained in Reference Example 3, 7 g of 1-bromo-3-chloropropane, 1.7 g of potassium iodide, 6.25 g of potassium carbonate and 70 ml of acetonitrile is heated under refluxing for 3 hours. The inorganic substances are filtered off, and the filtrate is concentrated under reduced pressure, and then the residue is treated with water and extracted with ethyl acetate. The organic layer is washed with water, dried and evaporated under reduced pressure. The residue is purified by column chromatography on silica gel (eluant: hexane:ethyl acetate=3:1), to give methyl 2-(3-chloropropyl)-3-oxo-3,4-dihydro-2H-1,5-benzodioxepin-2-carboxylate as a colorless oil. Mass spectrum m/e: 298, 300 (M+). IR $\nu_{max}^{neat}$ cm$^{-1}$: 1760, 1740. NMR (CDCl$_3$) δ: 3.66 (3H, singlet, OCH$_3$), 4.62 (2H, double doublet, C$_4$—H).

REFERENCE EXAMPLE 5

To a mixture of 2.5 g of methyl 2-(3-chloropropyl)-3-oxo-3,4-dihydro-2H-1,5-benzodioxepin-2-carboxylate obtained in Reference Example 4 in 20 ml of methanol, sodium borohydride is added in small portions with stirring and under ice-cooling. After completion of the reaction, the reaction mixture is treated with water and extracted with ethyl acetate. The organic layer is washed with water, dried, and evaporated under reduced pressure. The residue is purified by column chromatography on silica gel (eluant: hexane:ethyl acetate=3:1→1:1). From the first fraction eluted, 1.75 g of methyl 2-(3-chloropropyl)-3-hydroxy-3,4-dihydro-2H-1,5-benzodioxepin-2-carboxylate (A isomer) is obtained as a colorless oil. Mass spectrum m/e: 300, 302 (M+). IR $\nu_{max}^{neat}$ cm$^{-1}$: 3500(OH), 1755, 1735. NMR (CDCl$_3$) δ: 3.21 (4H, multiplet), 3.3 (2H, triplet, ClCH$_2$—), 3.70 (3H, singlet, OCH$_3$), 4.2 (3H, multiplet).

From the subsequent fraction eluted, 0.44 g of methyl 2-(3-chloropropyl)-3-hydroxy-3,4-dihydro-2H-1,5-benzodioxepin-2-carboxylate (B isomer) is obtained as a colorless oil. Mass spectrum m/e: 300, 302 (M+). IR $\nu_{max}^{neat}$ cm$^{-1}$: 3500 (OH), 1760, 1740. NMR (CDCl$_3$) δ: 1.9 (4H, multiplet), 3.42 (2H, triplet, ClCH$_2$—), 3.80 (3H, singlet, OCH$_3$).

REFERENCE EXAMPLE 6

To a mixture of 10 g of methyl 3-(2-hydroxyphenyl)propionate, 9.5 g of trimethylenediamine and 45 ml of N,N-dimethylformamide, a solution of 7.4 g of N,N-dimethylthiocarbamoyl chloride in 15 ml of N,N-dimethylformamide is added dropwise with stirring. After stirring for 15 hours at room temperature, the reaction mixture is poured into ice water and extracted with ethyl acetate. The organic layer is washed with water, dried, and evaporated under reduced pressure. The residue is purified by column chromatography on silica gel (eluant: hexane:ethyl acetate=4:1) to give 11 g of methyl 3-(2-N,N-dimethylthiocarbamoyloxyphenyl)propionate as a colorless oil. IR $\nu_{max}^{neat}$ cm$^{-1}$: 1735. NMR (CDCl$_3$) δ: 2.2–3.1 (4H, multiplet), 3.28, 3.38 (6H, 2 singlet N(CH$_3$)$_2$).

REFERENCE EXAMPLE 7

Methyl 3-(2-N,N-dimethylthiocarbamoyloxyphenyl)propionate obtained in Reference Example 6 (2.0 g) is stirred at 260°–270° C. for 30 minutes. After cooling, purification by column chromatography on silica gel (eluant: hexane:ethyl acetate=2:1) gives 1.4 g of methyl 3-(2-N,N-dimethylcarbamoylthiophenyl)propionate as a pale yellow oil. Mass spectrum m/e: 267 (M+). IR $\nu_{max}^{neat}$ cm$^{-1}$: 1735, 1670. NMR (CDCl$_3$) δ: 2.3–3.3 (4H, multiplet), 2.98 (6H, singlet, N(CH$_3$)$_2$), 3.58 (3H, singlet, OCH$_3$).

REFERENCE EXAMPLE 8

To a solution of 1.1 g of methyl 3-(2-N,N-dimethylcarbamoylthiophenyl)propionate obtained in Reference Example 7 in 10 ml of ethanol is added 0.58 g of potassium hydroxide, and the mixture is heated under refluxing for 5 hours. After cooling, the reaction mixture is concentrated under reduced pressure, and the residue is dissolved in 10 ml of water. To the solution are added 0.63 g of methyl bromoacetate and 2 ml of acetone and the mixture is stirred at room temperature for 4 hours. To the reaction mixture is added a solution of 0.62 g of dimethyl sulfate in 4 ml of acetone and the mixture is stirred at 60° C. for 15 hours. The reaction mixture is concentrated under reduced pressure and the residue is treated with water, and extracted with ethyl acetate. The organic layer is washed with water, dried, and evaporated under reduced pressure. The residue is purified by column chromatography on silica gel (eluant: hexane:ethyl acetate=3:1) to give 0.6 g of methyl 3-(2-methoxycarbonylmethylthiophenyl)propionate as a colorless oil. Mass spectrum m/e: 268(M+). IR $\nu_{max}^{neat}$ cm$^{-1}$: 1740. NMR (CDCl$_3$) δ: 2.4–3.3 (4H, multiplet), 3.62, 3.64 (6H, 2 singlet, OCH$_3$).

REFERENCE EXAMPLE 9

To a suspension of 0.8 g of 60% oily sodium hydride in 50 ml of toluene is added 0.05 ml of tert-butanol. To the resulting mixture, a solution of 2.1 g of methyl 3-(2-methoxycarbonylmethylthiophenyl)propionate obtained in Reference Example 8 in 50 ml of toluene is added in small portions at 130° C. under nitrogen atmosphere (for 8 hours). After cooling, 2 ml of acetic acid is added and the precipitates are filtered off. The filtrate is concentrated under reduced pressure and the residue is purified by column chromatography on silica gel (eluant: hexane:ethyl acetate=4:1) to give 1.5 g of methyl 3-oxo-2,3,4,5-tetrahydro-1-benzothiepin-2-carboxylate as a colorless oil. Mass spectrum m/e: 236 (M+). IR $\nu_{max}^{neat}$ cm$^{-1}$: 1740, 1700. NMR (CDCl$_3$) δ: 2.6–3.4 (4H, multiplet), 3.62 (3H, singlet, OCH$_3$), 4.2 (1H, singlet, C$_2$—H).

REFERENCE EXAMPLE 10

A mixture of 1.5 g of methyl 3-oxo-2,3,4,5-tetrahydro-1-benzothiepin-2-carboxylate obtained in Reference Example 9 and 3.0 g of 1-bromo-3-chloropropane, 0.5 g of potassium iodide, 1.7 g of potassium carbonate and 20 ml of acetonitrile is stirred at 80°–85° C. for 5 hours. After cooling, the inorganic substances are filtered off, and the filtrate is concentrated under reduced pressure, and then the residue is treated with water, and extracted with ethyl acetate. The organic layer is washed with ether, dried, and evaporated under reduced pressure. The residue is purified by column chromatography on silica gel (eluant: hexane:methylene chloride:ethyl acetate=15:10:1) to give 1.1 g of methyl 2-(3-chloropropyl)-3-oxo-2,3,4,5-tetrahydro-1-benzothiepin-2-carboxylate as a colorless oil. Mass spectrum m/e: 312, 314 (M+). IR $\nu_{max}^{neat}$ cm$^{-1}$: 1720. NMR (CDCl$_3$) δ: 1.7–3.6 (10H, multiplet), 3.65 (3H, singlet, OCH$_3$).

REFERENCE EXAMPLE 11

To a solution of 1.0 g of methyl 2-(3-chloropropyl)-3-oxo-2,3,4,5-tetrahydro-1-benzothiepin-2-carboxylate obtained in Reference Example 10 in a mixture of 3 ml of tetrahydrofuran and 12 ml of methanol, 0.1 g of sodium borohydride is added in small portions with stirring and under ice-cooling. The reaction mixture is poured into ice water and extracted with ethyl acetate. The organic layer is washed with water, dried, and evaporated under reduced pressure. The residue is purified by column chromatography on silica gel (eluant: hexane:ethyl acetate=2:1), to give 0.8 g of methyl cis-2-(3-chloropropyl)-3-hydroxy-2,3,4,5-tetrahydro-1-benzothiepin-2-carboxylate as an oil. Recrystallization from ethyl acetate gives colorless prisms: m.p. 108°–110° C. (assigned to cis-isomer by X-ray analysis)

Elementary analysis for C$_{15}$H$_{19}$ClO$_3$S: Calculated: C, 57.23; H, 6.08. Found: C, 57.27; H, 6.11.

IR $\nu_{max}^{KBr}$ cm$^{-1}$: 3500 (OH), 1730.

REFERENCE EXAMPLE 12

To a mixture of 11 g of methyl 3-(2-hydroxy-4-methoxyphenyl)propionate, 9.5 g of trimethylenediamine and 45 ml of N,N-dimethylformamide, a solution of 7.5 g of N,N-dimethylthiocarbamoyl chloride in 15 ml of N,N-dimethylformamide is added dropwise with stirring. After stirring for 13 hours at room temperature, the reaction mixture is poured into ice water and extracted with ethyl acetate. The organic layer is washed with water, dried over anhydrous sodium sulfate, and evaporated under reduced pressure. The residue is stirred at 280°–290° C. for one hour. After cooling, the reaction mixture is dissolved in 60 ml of ethanol and 3.6 g of potassium hydroxide is added to the solution. The mixture is heated under refluxing for 5 hours, and then 3.9 g of methyl bromoacetate is added. The resulting mixture is stirred at room temperature for 4 hours, and 4.0 g of dimethyl sulfate and 30 ml of acetone are added to the mixture. The reaction mixture is stirred at 60° C. for 10 hours, and then concentrated under reduced pressure. The residue is treated with water, and extracted with ethyl acetate. The organic layer is washed with water, dried, and then concentrated under reduced pressure. The residue is purified by column chromatography on silica gel (eluant: hexane:ethyl acetate=2:1), to give 4.0 g of methyl 3-(4-methoxy-2-methoxycarbonylmethylthiophenyl)propionate. To a suspension of 0.8 g of 60% oily sodium hydride in 50 ml of toluene is added 0.05 ml of tert-butanol. To the resulting mixture, a solution of 2.2 g of methyl 3-(4-methoxy-2-methoxycarbonylmethylthiophenyl)propionate in 50 ml of toluene is added dropwise at 130° C. under nitrogen atmosphere (8 hours). After cooling, 2 ml of acetic acid is added to the reaction mixture and the resulting mixture is stirred. The precipitates are filtered off and the filtrate is concentrated under reduced pressure. The residue is purified by column chromatography on silica gel (eluant: hexane:ethyl acetate=3:1) to give 1.3 g of methyl 8-methoxy-3-oxo-2,3,4,5-tetrahydro-1-benzothiepin-2-carboxylate. A mixture of 1.0 g of methyl 8-methoxy-3-oxo-2,3,4,5-tetrahydro-1-benzothiepin-2-carboxylate, 2.5 g of 1-bromo-3-chloropropane, 0.3 g of potassium iodide, 1.5 g of potassium carbonate and 20 ml of acetonitrile is stirred at 85° C. for 5 hours. After cooling, the inorganic substances are filtered off, and the filtrate is concentrated under reduced pressure. The resulting residue is purified by column chromatography on silica gel (eluant: hexane:methylene chloride:ethyl acetate=15:10:1), to give 0.9 g of methyl 2-(3-chloropropyl)-8-methoxy-3-oxo-2,3,4,5-tetrahydro-1-benzothiepin-2-carboxylate. To a solution of 0.7 g of methyl 2-(3-chloropropyl)-8-methoxy-3-oxo-2,3,4,5-tetrahydro-1-benzothiepin-2-carboxylate in a mixture of 10 ml of methanol and 3 ml of tetrahydrofuran, 0.1 g of sodium borohydride is added in small portions with stirring and under ice-cooling. After stirring for 1 hour, the reaction mixture is poured into ice water and extracted with ethyl acetate. The organic layer is washed with water, dried, and evaporated under reduced pressure. The residue is purified by column chromatography (eluant: hexane:ethyl acetate=2:1), to give methyl 2-(3-chloropropyl)-3-hydroxy-8-methoxy-2,3,4,5-tetrahydro-1-benzothiepin-2-carboxylate.

REFERENCE EXAMPLE 13

A solution of 15 g of methyl 3-(4-methoxy-2-methoxy-carbonylmethyloxyphenyl)propionate in 200 ml of toluene is added dropwise to a suspension of 5.6 g of 60% oily sodium hydride in 200 ml of toluene to which 0.4 ml of tert-butanol is added, for a period of 8 hours with heating under refluxing. The reaction mixture is heated under refluxing for 30 minutes and allowed to stand overnight, and then poured into ice water containing 10 ml of acetic acid. The organic layer is separated, washed with water, dried and evaporated under reduced pressure. The residue is purified by column chromatography on silica gel (eluant: hexane:ethyl acetate=4:1) to give 9.5 g of methyl 8-methoxy-3-oxo-2,3,4,5-tetrahydro-1-benzoxepin-2-carboxylate as a colorless oil. A mixture of 7.4 g of methyl 8-methoxy-3-oxo-2,3,4,5-tetrahydro-1-benzoxepin-2-carboxylate, 10.9 g of 1-bromo-3-chloropropane, 1.5 g of potassium iodide, 10 g of anhydrous potassium carbonate and 300 ml of acetonitrile is heated under refluxing with stirring for 5 hours. After cooling, the inorganic substances are filtered off and the filtrate is concentrated under reduced pressure. The residue is purified by column chromatography on silica gel (eluant: hexane:ethyl acetate=8:1) to give 9 g of methyl 2-(3-chloropropyl)-8-methoxy-3-oxo-2,3,4,5-tetrahydro-1-benzoxepin-2-carboxylate as an oil. In 100 ml of methanol is dissolved 9 g of methyl 2-(3-chloropropyl)-8-methoxy-3-oxo-2,3,4,5-tetrahydro-1-benzoxepin-2-carboxylate, and 0.6 g of sodium borohydride is added in small portions to the solution under ice-cooling with stirring. The reaction mixture is concentrated under reduced pressure, and the residue is treated with water and extracted with ethyl acetate. The organic layer is washed with water, dried and evaporated under reduced pressure, and the residue is purified by column chromatography on silica gel (eluant: hexane:ethyl acetate=3:1) to give 3.3 g of methyl trans-2-(3-chloropropyl)-3-hydroxy-8-methoxy-2,3,4,5-tetrahydro-1-benzoxepin-2-carboxylate as a colorless oil from the first fraction eluted.

IR spectrum $\nu_{max}^{film}$ cm$^{-1}$: 3500 (OH), 1740 (C=O). Mass spectrum m/e: 328, 330 (M+).

From the subsequent fraction eluted, 3.4 g of methyl cis-2-(3-chloropropyl)-3-hydroxy-8-methoxy-2,3,4,5-tetrahydro-1-benzoxepin-2-carboxylate is obtained as an oil.

IR spectrum $\nu_{max}^{film}$ cm$^{-1}$: 3500 (OH), 1700 (C=O). Mass spectrum m/e: 328, 330 (M+).

EXAMPLE 1

A mixture of 0.5 g of methyl 2-(3-chloropropyl)-3-oxo-2,3,4,5-tetrahydro-1-benzoxepin-2-carboxylate obtained in Reference Example 1, 0.6 g of N-phenylpiperazine and 0.27 g of potassium iodide is heated at 85° C. for 3 hours. After cooling, water is added and the mixture is extracted with ethyl acetate. The organic layer is washed with water, dried, and evaporated under reduced pressure. The residue is purified by column chromatography on silica gel (eluant: hexane:ethyl acetate=2:1→1:1), to give 0.55 g of methyl 3-oxo-2-[3-(4-phenyl-1-piperazinyl)propyl]-2,3,4,5-tetrahydro-1-benzoxepin-2-carboxylate as a colorless oil. Recrystallization from ethanol-ether of the hydrochloride obtained by treatment with ethanolic hydrochloric acid gives 0.5 g of colorless needles: m.p. 165°-167° C.

Elementary analysis for $C_{25}H_{30}N_2O_4 \cdot 2HCl \cdot \frac{1}{4}H_2O$: Calculated: C, 60.06; H, 6.55; N, 5.60. Found: C, 59.86; H, 6.36; N, 5.45.

EXAMPLE 2

A mixture of 0.15 g of methyl 2-(3-chloropropyl)-3-oxo-2,3,4,5-tetrahydro-1-benzothiepin-2-carboxylate obtained in Reference Example 10, 0.18 g of N-phenylpiperazine and 0.1 g of potassium iodide is stirred at 85°-90° C. for 4 hours. The reaction mixture is treated with water and extracted with ethyl acetate. The organic layer is washed with water, dried, and evaporated under reduced pressure. The residue is purified by column chromatography on silica gel (eluant: hexane:ethyl acetate=2:1), to give 70 mg of methyl 3-oxo-2-[3-(4-phenyl-1-piperazinyl)propyl]-2,3,4,5-tetrahydro-1-benzothiepin-2-carboxylate as crystals. Recrystallization from ethyl acetate-hexane gives colorless needles: m.p. 101°-103° C.

Elementary analysis for $C_{25}H_{30}N_2O_3S$: Calculated: C, 68.46; H, 6.89; N, 6.39. Found: C, 68.44; H, 6.84; N, 6.51.

EXAMPLE 3

A mixture of 0.9 g of methyl 2-(3-chloropropyl)-3-hydroxy-2,3,4,5-tetrahydro-1-benzoxepin-2-carboxylate (A isomer) obtained in Reference Example 2, 1.07 g of N-phenylpiperazine and 0.6 g of potassium iodide is stirred at 90° C. for 3 hours. After cooling, the reaction mixture is treated with water and extracted with ethyl acetate.

The organic layer is washed with water, dried, and evaporated under reduced pressure. The residue is purified by column chromatography on silica gel (eluant: hexane:ethyl acetate=3:1→1:3), to give 0.68 g of methyl 3-hydroxy-2-[3-(4-phenyl-1-piperazinyl)propyl]-2,3,4,5-tetrahydro-1-benzoxepin-2-carboxylate (A isomer) as crystals. Recrystallization from ethyl acetate-hexane gives colorless needles: m.p. 98°-99° C.

Elementary analysis for $C_{25}H_{30}N_2O_4$: Calculated: C, 70.73; H, 7.60; N, 6.60. Found: C, 70.83; H, 7.63; N, 6.51.

EXAMPLE 4

A mixture of 0.36 g of methyl 2-(3-chloropropyl)-3-hydroxy-2,3,4,5-tetrahydro-1-benzoxepin-2-carboxylate (B isomer) obtained in Reference Example 2, 0.43 g of N-phenylpiperazine and 0.2 g of potassium iodide is stirred at 90° C. for 3 hours and treated in the same manner as shown in Example 3, to give 0.18 g of methyl 3-hydroxy-2-[3-(4-phenyl-1-piperazinyl)propyl]-2,3,4,5-tetrahydro-1-benzoxepin-2-carboxylate (B isomer) as crystals. Recrystallizatiion from ethyl acetate-hexane gives colorless needles: m.p. 112°-113° C.

Elementary analysis for $C_{25}H_{32}N_2O_4$: Calculated: C, 70.73; H, 7.60; N, 6.60. Found: C, 70.99; H, 7.74; N, 6.49.

EXAMPLE 5

A mixture of 0.5 g of methyl 2-(3-chloropropyl)-3-hydroxy-3,4-dihydro-2H-1,5-benzodioxepin-2-carboxylate (A isomer) obtained in Reference Example 5, 0.54 g of N-phenylpiperazine and 0.28 g of potassium iodide is stirred at 90° C. for 3 hours and treated in the same manner as shown in Example 3, to give 0.43 g of methyl 3-hydroxy-2-[3-(4-phenyl-1-piperazinyl)propyl]-3,4-dihydro-2H-1,5-benzodioxepin-2-carboxylate as crystals. Recrystallization from ethyl acetate-hexane gives white crystals: m.p. 143°-144° C.

Elementary analysis for $C_{24}H_{30}N_2O_5 \cdot \frac{1}{4}H_2O$: Calculated: C, 66.87; H, 7.13; N, 6.50. Found: C, 66.94; H, 6.97; N, 6.47.

EXAMPLE 6

A mixture of 0.44 g of methyl 2-(3-chloropropyl)-3-hydroxy-3,4-dihydro-2H-1,5-benzodioxepin-2-carboxylate (B isomer) obtained in Reference Example 5, 0.5 g of N-phenylpiperazine and 0.25 g of potassium iodide is stirred at 90° C. for 3 hours. The reaction mixture is treated in the same manner as shown in Example 3, to give 0.33 g of methyl 3-hydroxy-2-[3-(4-phenyl-1-piperazinyl)propyl]-3,4-dihydro-2H-1,5-benzodioxepin-2-carboxylate (B isomer) as crystals. Recrystallization from ethyl acetate-hexane gives white crystals: m.p. 113°–115° C.

Elementary analysis for $C_{24}H_{30}N_2O_5$: Calculated: C, 67.59; H, 7.09; N, 6.57. Found: C, 67.48; H, 7.04; N, 6.62.

EXAMPLE 7

A mixture of 0.3 g of methyl cis-2-(3-chloropropyl)-3-hydroxy-2,3,4,5-tetrahydro-1-benzothiepin-2-carboxylate obtained in Reference Example 11, 0.37 g of N-phenylpiperazine and 0.15 g of potassium iodide is stirred at 85°–90° C. for 6 hours. The reaction mixture is treated in the same manner as shown in Example 3, to give 0.25 g of methyl cis-3-hydroxy-2-[3-(4-phenyl-1-piperazinyl)propyl]-2,3,4,5-tetrahydro-1-benzothiepin-2-carboxylate as crystals. Recrystallization from ethyl acetate-hexane gives colorless prisms: m.p. 152°–154° C.

Elementary analysis for $C_{25}H_{32}N_2O_3S$: Calculated: C, 68.15; H, 7.32; N, 6.36. Found: C, 68.40; H, 7.34; N, 6.36.

EXAMPLE 8

To a solution of 0.2 g of methyl 3-oxo-2-[3-(4-phenyl-1-piperazinyl)propyl]-2,3,4,5-tetrahydro-1-benzothiepin-2-carboxylate obtained in Example 2 in 20 ml of methanol, 50 mg of sodium borohydride is added in small portions with stirring. After stirring for one hour, the reaction mixture is treated with water and extracted with ethyl acetate. The organic layer is washed with water, dried, and evaporated under reduced pressure. The residue is recrystallized from ethyl acetate-hexane, to give 0.15 g of methyl 3-hydroxy-2-[3-(4-phenyl-1-piperazinyl)propyl]-2,3,4,5-tetrahydro-1-benzothiepin-2-carboxylate as crystals, obtained in Example 7: m.p. 152°–154° C.

EXAMPLE 9

A mixture of 0.3 g of methyl 2-(3-chloropropyl)-3-hydroxy-2,3,4,5-tetrahydro-1-benzoxepin-2-carboxylate (B isomer) obtained in Reference Example 2, 0.4 g of N-methyl-3,4-dimethoxyphenethylamine and 0.1 g of potassium iodide is stirred at 90° C. for 3 hours, and treated in the same manner as shown in Example 3, to give methyl 3-hydroxy-2-[3-(N-methyl-3,4-dimethoxyphenethylamino)propyl]-2,3,4,5-tetrahydro-1-benzoxepin-2-carboxylate, which is converted into the hydrochloride as white powders.

Elementary analysis for $C_{26}H_{35}NO_6.2HCl.\frac{1}{2}H_2O$: Calculated: C, 57.88; H, 7.10; N, 2.60. Found: C, 57.76; H, 6.92; N, 2.71.

EXAMPLE 10

A mixture of 0.3 g of methyl 2-(3-chloropropyl)-3-hydroxy-8-methoxy-2,3,4,5-tetrahydro-1-benzothiepin-2-carboxylate obtained in Reference Example 12, 0.5 g of N-phenylpiperazine and 0.1 g of potassium iodide is stirred at 90° C. for 5 hours. The reaction mixture is treated in the same manner as shown in Example 3, to give methyl 3-hydroxy-8-methoxy-2-[3-(4-phenyl-1-piperazinyl)propyl]-2,3,4,5-tetrahydro-1-benzothiepin-2-carboxylate. The hydrochloride of this product is white powders.

Elementary analysis as $C_{26}H_{34}N_2O_4S.2HCl.\frac{1}{2}H_2O$: Calculated: C, 60.00; H, 7.17; N, 5.38. Found: C, 59.83; H, 7.25; N, 5.21.

EXAMPLE 11

A mixture of 0.7 g of methyl 2-(3-chloropropyl)-3-hydroxy-8-methoxy-2,3,4,5-tetrahydro-1-benzothiepin-2-carboxylate obtained in Reference Example 12, 0.5 g of N-(4-hydroxyphenyl)piperazine and 2 ml of N,N-dimethylacetamide is stirred at 90° C. for 6 hours. The reaction mixture is treated with water and extracted with ethyl acetate, and the organic layer is washed with water, dried and evaporated under reduced pressure. The residue is purified by column chromatography on silica gel (eluant: hexane:ethyl acetate:methanol=20:20:1) and recrystallized from ethyl acetate to give 0.3 g of methyl 3-hydroxy-2-[3-[4-(4-hydroxyphenyl)-1-piperazinyl]propyl]-8-methoxy-2,3,4,5-tetrahydro-1-benzothiepin-2-carboxylate as colorless needles: m.p. 120°–124° C. (recrystallized from ethyl acetate).

Elementary analysis for $C_{26}H_{34}N_2O_5S.H_2O$: Calculated: C, 61.88; H, 7.19; N, 5.55. Found: C, 61.81; H, 7.24; N, 5.71.

EXAMPLE 12

A mixture of 1.0 g of methyl trans-2-(3-chloropropyl)-3-hydroxy-8-methoxy-2,3,4,5-tetrahydro-1-benzoxepin-2-carboxylate, 1.1 g of N-phenylpiperazine and 0.25 g of potassium iodide is stirred at 90° C. for 2.5 hours. The reaction mixture is treated with water and extracted with ethyl acetate, and the organic layer is washed with water, dried and evaporated under reduced pressure. The residue is purified by column chromatography on silica gel (eluant: hexane:ethyl acetate:methanol=30:20:1) to give 1.0 g of methyl trans-3-hydroxy-8-methoxy-2-[3-(4-phenyl-1-piperazinyl)propyl]-2,3,4,5-tetrahydro-1-benzoxepin-2-carboxylate as a pale yellow oil, which is converted to the hydrochloride as white crystals: m.p. 140°–155° C. (decomposition).

Elementary analysis for $C_{26}H_{34}N_2O_5.2HCl$: Calculated: C, 59.20; H, 6.88; N, 5.31. Found: C, 59.12; H, 6.96; N, 5.23.

EXAMPLE 13

A mixture of 1.0 g of methyl cis-2-(3-chloropropyl)-3-hydroxy-8-methoxy-2,3,4,5-tetrahydro-1-benzoxepin-2-carboxylate, 1.1 g of N-phenylpiperazine and 0.25 g of potassium iodide is stirred at 90° C. for 2.5 hours, and treated in the same manner as shown in Example 12 to give methyl cis-3-hydroxy-8-methoxy-2-[3-(4-phenyl-1-piperazinyl)propyl]-2,3,4,5-tetrahydro-1-benzoxepin-2-carboxylate (assigned to cis-isomer by X-ray analysis) as colorless prisms: m.p. 126°–128° C. (recrystallized from ethyl acetate-hexane).

Elementary analysis for $C_{26}H_{34}N_2O_5$: Calculated: C, 68.70; H, 7.54; N, 6.16. Found: C, 68.42; H, 7.62; N, 6.02.

EXAMPLE 14

A mixture of 0.7 g of methyl cis-2-(3-chloropropyl)-3-hydroxy-8-methoxy-2,3,4,5-tetrahydro-1-benzoxepin-2-carboxylate, 0.5 g of N-(4-hydroxyphenyl)piperazine and 2 ml of N,N-dimethylacetamide is stirred at 90° C.

for 6 hours. The mixture is treated with water and extracted with ethyl acetate, and the organic layer is washed with water, dried and evaporated under reduced pressure. The residue is purified by column chromatography on silica gel (eluant: hexane:ethyl acetate:methanol=20:20:1) to give methyl cis-3-hydroxy-2-[3-[4-(4-hydroxyphenyl)-1-piperazinyl]propyl]-8-methoxy-2,3,4,5-tetrahydro-1-benzoxepin-2-carboxylate as a viscous oil, which is converted to the hydrochloride as white powders.

Elementary analysis for $C_{26}H_{34}N_2O_6 \cdot 2HCl \cdot H_2O$: Calculated: C, 55.61; H, 6.82; N, 4.99. Found: C, 55.78; H, 7.13; N, 4.78.

PREPARATION EXAMPLE

The compound (I) of this invention can be used for example as a therapeutic for ischemic cardiopathies, in the following example of formulation.

| 1. Tablet | | |
|---|---|---|
| (1) methyl 3-hydroxy-2-[3-(4-phenyl-1-piperazinyl)-propyl]-2,3,4,5-tetrahydro-1-benzothiepin-2-carboxylate | 10 g | for 1000 tablets, 130 g |
| (2) lactose | 90 g | |
| (3) corn starch | 29 g | |
| (4) magnesium stearate | 1 g | |

Ingredients (1) and (2) and 17 g of (3) are mixed and granulated together with a paste prepared from 7 g of ingredient (3). To the granules 5 g of ingredient (3) and ingredient (4) are added, and the mixture is compressed by compressor to produce 1000 tablets of 7 mm in diameter containing 10 mg of ingredient (1) in a tablet.

EFFECT OF THE INVENTION

Experiment 1

Serotonin $S_2$-receptor blocking activity of the compound (I) of this invention (in vitro)

Experimental method

The experiment was carried out according to the method of Bevan & Osher (Agents Actions, Vol. 2, p. 257, 1972) with a few modifications. The heart removed from a hog immediately after being slaughtered at a slaughterhouse was preserved under ice-cooling, and the left circumflexus coronary artery was dissected within 3 hours. The coronary artery was cut into a ring preparation of about 3 mm in width, which was suspended in a double-wall organ bath containing 20 ml of Krebs-Henseleit solution using a pair of suspending hooks. One of the suspending hooks was fixed to the bottom of the organ bath, while the other was connected to a straingaige transducer, and the constriction of the ring preparation of the porcine coronary artery was isometrically measured and recorded on a polygraph recorder. The organ bath was maintained at 37° C., and the Krebs-Henseleit solution was saturated with a mixed gas of 97% $O_2$+3% $CO_2$. The composition of the Krebs Henseleit solution was: NaCl 118.3 mM, KCl 4.7 mM, $KH_2PO_4$ 1.2 mM, $CaCl_2 \cdot 2H_2O$ 2.58 mM, $MgSO_4 \cdot 7H_2O$ 1.15 mM, $NaHCO_3$ 25 mM, and glucose 11.1 mM.

In 1 or 2 hours when the blood vessel preparation showed stable resting tension, the resting tension was readjusted to be 2 g, and $10^6$M serotonin (final concentration) was added to the organ bath at the interval of about one hour to check the responsiveness of the preparation. When the reaction of the blood vessel to 2 to 3 additions of serotonin became stable, the test compound of various concentration was added to the organ bath 10 minutes prior to subsequent addition of serotonin. From the magnitudes of contraction caused by serotonin before and after the addition of the test compound, the serotonergic blocking effect of the test compound was calculated. Experimental results The results of the experiment is shown in Table 2.

TABLE 2

Serotonin $S_2$-receptor blocking effect in porcine coronary artery preparation

| No. of Example | Concentration (M) | Inhibition of serotonin-induced constriction (%) |
|---|---|---|
| 1 | $10^{-5}$ | 100 |
| 2 | $10^{-5}$ | 100 |
| 3 | $10^{-5}$ | 100 |
| 4 | $10^{-5}$ | 59.1 |
| 5 | $10^{-5}$ | 95.0 |
| 6 | $10^{-5}$ | 93.3 |
| 7 | $10^{-5}$ | 95.5 |
| 10 | $10^{-6}$ | 69 |
| 11 | $10^{-6}$ | 100 |
| 12 | $10^{-5}$ | 100 |
| 13 | $10^{-5}$ | 100 |
| 14 | $10^{-6}$ | 52 |

What is claimed is:

1. A compound of the formula:

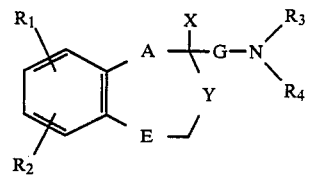

wherein $R_1$ and $R_2$ are independently hydrogen, halogen, hydroxy, $C_{1-4}$ alkyl or $C_{1-4}$ alkoxy, $R_3$ and $R_4$, taken together with the nitrogen atom, form 4-phenylpiperazinyl in which the phenyl group is unsubstituted or substituted by hydroxy, X is (1) hydrogen, (2) $C_{1-4}$ alkyl, (3) $C_{1-4}$ alkanoyl, (4) hydroxymethyl, (5) $C_{1-5}$ alkanoyloxymethyl, (6) phenyl-$C_{1-4}$ alkyl which may be substituted by 1 to 3 members of halogen, $C_{1-4}$ alkyl, $C_{1-4}$ alkoxy, methylenedioxy, amino, nitro or hydroxy, (7) phenyl which may be substituted by 1 to 3 members of halogen, $C_{1-4}$ alkyl, $C_{1-4}$ alkoxy, methylenedioxy, amino, nitro or hydroxy, (8) $C_{1-4}$ alkoxycarbonyl, (9) phenyl-$C_{1-4}$ alkoxycarbonyl, (10) carbamoyl which may be substituted by 1 or 2 members of $C_{1-4}$ alkyl, phenyl or phenyl-$C_{1-4}$ alkyl or (11) carboxy, Y is $>C=O$ or $>CH-OR_5$ in which $R_5$ is (i) hydrogen, (ii) $C_{1-6}$ alkanoyl, (iii) phenyl-$C_{1-6}$ alkanoyl unsubstituted or substituted by 1 to 3 members of halogen, $C_{1-4}$ alkyl, $C_{1-4}$ alkoxy, methylenedioxy, amino, nitro or hydroxy, (iv) carbamoyl unsubstituted or substituted by (1) $C_{1-4}$ alkyl, (2) phenyl unsubstituted or substituted by 1 to 3 members of halogen, $C_{1-4}$ alkyl, $C_{1-4}$ alkoxy, methylenedioxy, amino, nitro or hydroxy or (3) phenyl-$C_{1-4}$ alkyl unsubstituted or substituted by 1 to 3 members of halogen, $C_{1-4}$ alkyl, $C_{1-4}$ alkoxy, methylenedioxy, amino, nitro or hydroxy, A is oxygen atom or sulfur atom, E is oxygen atom or methylene, and G is $C_{1-6}$ alkylene, provided that when A is sulfur atom, E is methylene, or a pharmaceutically acceptable salt thereof.

2. A compound according to claim 1, of the formula:

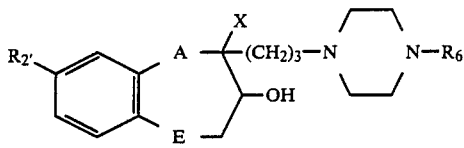

wherein $R_6$ is phenyl being unsubstituted or substituted by hydroxy, $R_{2'}$ is hydrogen or $C_{1-4}$ alkoxy, X is $C_{1-4}$ alkoxycarbonyl, A is oxygen atom or sulfur atom, and E is oxygen atom or methylene, provided that when A is sulfur atom, E is methylene, or a pharmaceutically acceptable salt thereof.

3. A compound according to claim 2, wherein $R_6$ is phenyl.

4. A compound according to claim 1, wherein $R_1$ and $R_2$ are independently hydrogen or $C_{1-4}$ alkoxy.

5. A compound according to claim 1, wherein $R_3$ and $R_4$, taken together with the nitrogen atom, form 4-phenylpiperazinyl.

6. A compound according to claim 1, wherein X is $C_{1-4}$ alkoxycarbonyl.

7. A compound according to claim 1, wherein Y is $>C=O$ or $>CH-OR_5$ in which $R_5$ is hydrogen.

8. A compound according to claim 1, wherein Y is hydroxymethylene.

9. A compound according to claim 1, wherein $R_1$ is hydrogen and $R_2$ is hydrogen or $C_{1-4}$ alkoxy.

10. A compound according to claim 1, wherein G is trimethylene.

11. A compound according to claim 1, which is methyl 3-hydroxy-2-[3-(4-phenyl-1-piperazinyl)propyl]-2,3,4,5-tetrahydro-1-benzothiepin-2-carboxylate.

12. A compound according to claim 1, which is methyl 3-hydroxy-8-methoxy-2-[3-(4-phenyl-1-piperazinyl)propyl]-2,3,4,5-tetrahydro-1-benzothiepin-2-carboxylate.

13. A compound according to claim 1, which is methyl 3-hydroxy-2-[3-[4-(4-hydroxyphenyl)-1-piperazinyl]propyl]-8-methoxy-2,3,4,5-tetrahydro-1-benzothiepin-2-carboxylate.

14. A compound according to claim 1, which is methyl 3-hydroxy-8-methoxy-2-[3-(4-phenyl-1-piperazinyl)propyl]-2,3,4,5-tetrahydro-1-benzoxepin-2-carboxylate.

15. A compound according to claim 1, which is methyl 3-hydroxy-2-[3-[4-(4-hydroxyphenyl)-1-piperazinyl]propyl]-8-methoxy-2,3,4,5-tetrahydro-1-benzoxepin-2-carboxylate.

* * * * *